United States Patent [19]

Schnur

[11] Patent Number: 4,812,471

[45] Date of Patent: Mar. 14, 1989

[54] HYPOGLYCEMIC 5-(ISOXAZOLYL OR ISOTHIAZOLYL)-OXAZOLIDINE-2,4-DIONES

[75] Inventor: Rodney C. Schnur, Noank

[73] Assignee: Pfizer Inc., New York, N.Y.

[21] Appl. No.: 153,622

[22] Filed: Feb. 8, 1988

Related U.S. Application Data

[60] Division of Ser. No. 55,498, May 28, 1987, Pat. No. 4,753,956, which is a division of Ser. No. 783,982, Oct. 3, 1985, Pat. No. 4,689,536, which is a division of Ser. No. 574,236, Jan. 26, 1984, Pat. No. 4,565,820, which is a division of Ser. No. 380,176, May 20, 1982, Pat. No. 4,431,810, which is a division of Ser. No. 252,962, Apr. 23, 1981, Pat. No. 4,342,771, which is a continuation-in-part of Ser. No. 222,202, Jan. 2, 1981, Pat. No. 4,367,234, which is a continuation-in-part of Ser. No. 173,206, Jul. 28, 1980, abandoned.

[51] Int. Cl.$^4$ .................... A61K 31/41; A61K 31/42; C07D 263/44; C07D 275/02

[52] U.S. Cl. .................... 514/372; 514/376; 548/214; 548/226; 548/232

[58] Field of Search ............ 514/372, 376; 548/214, 548/226, 232

[56] References Cited

U.S. PATENT DOCUMENTS

| | | | |
|---|---|---|---|
| 2,338,220 | 1/1944 | Wallingford | 548/226 |
| 2,721,197 | 8/1955 | Sheehan | 540/304 |
| 3,699,229 | 10/1972 | Poltnikoff | 514/376 |
| 4,220,787 | 9/1980 | Scholz | 548/226 |
| 4,717,725 | 1/1988 | York | 514/376 |

FOREIGN PATENT DOCUMENTS

| | | | |
|---|---|---|---|
| 3115650 | 11/1982 | Fed. Rep. of Germany | 548/226 |
| 59-216882 | 12/1984 | Japan | 548/226 |
| 869807 | 6/1961 | United Kingdom | 548/226 |

OTHER PUBLICATIONS

Ciamacian and Silber, Ber. 19, pp. 1708–1714 (1886).
Clark-Lewis, Chem. Rev. 58, pp. 63–99 (1958).
Brink and Freeman, J. Neuro. Chem. 19 (7), pp. 1783–1788 (1972).

*Primary Examiner*—Donald G. Gaus
*Assistant Examiner*—Mark W. Noel
*Attorney, Agent, or Firm*—Peter C. Richardson; J. Trevor Lumb; Robert K. Blackwood

[57] ABSTRACT

Hypoglycemic 5-chromanyl, 2,3-dihydro-5-benzo[b]-furanyl, 5-pyridyl, 5-quinolyl, 5-pyrrolyl, 5-indolyl, 5-thiazolyl, 5-oxazolyl, 5-isothiazolyl and 5-isoxazolyl oxazolidine-2.4-diones and the pharmacetically-acceptable salts thereof; certain 3-acylated derivatives thereof; a method of treating hyperglycemic animals therewith; and intermediates useful in the preparation of said compounds.

4 Claims, No Drawings

HYPOGLYCEMIC 5-(ISOXAZOLYL OR ISOTHIAZOLYL)-OXAZOLIDINE-2,4-DIONES

CROSS REFERENCE TO RELATED APPLICATION

This application is a division of copending application Ser. No. 07/055,498, filed May 28, 1987, now U.S. Pat. No. 4,753,956, which is a division of Ser. No. 783,982, filed Oct. 3, 1985, now U.S. Pat. No. 4,689,336, which is a division of Ser. No. 574,236, filed Jan. 26, 1984, now U.S. Pat. No. 4,565,820, which is a division of application Ser. No. 380,176, filed May 20, 1982, now U.S. Pat. No. 4,431,810, which is a division of application Ser. No. 252,962, Apr. 23, 1981, now U.S. Pat. No. 4,342,771, which is a continuation-in-part of copending application Ser. No. 222,202, filed Jan. 2, 1981 now U.S. Pat. No. 4,367,234 which is a continuation-in-part of application Ser. No. 173,206, filed July 28, 1980, now abandoned.

BACKGROUND OF THE INVENTION

The present invention relates to certain 5-chromanyl, 2,3-dihydrobenzo[b]furanyl, 5-pyridyl, 5-quinolyl, 5-pyrrolyl, 5-indolyl, 5-thiazolyl, 5-oxazolyl, 5-isothiazolyl and 5-isoxazolyl derivatives of oxazolidine-2,4-dione having utility as hypoglycemic agents.

In spite of the early discovery of insulin and its subsequent wide-spread use in the treatment of diabetes, and the later discovery and use of sulfonylureas (e.g., chlorpropamide, tolbutamide, acetohexamide, tolazamide) and biguanides (e.g., phenformin) as oral hypoglycemic agents, the treatment of diabetes remains less than satisfactory. The use of insulin, necessary in a high percentage of diabetics where available synthetic hypoglycemic agents are not effective, requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Where effective, a synthetic hypoglycemic agent is preferred over insulin, being more convenient to administer and less prone to cause severe hypoglycemic reactions. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057–1080].

The oxazolidine-2,4-diones of the present invention are novel compounds; this in spite of the fact that the oxazolidine-2,4-diones are broadly known as a class of compounds [for an extensive review, see Clark-Lewis, Chem. Rev. 58, pp. 63–99 (1958)]. Among the compounds known in this class are 5-phenyloxazolidine-2,4-dione, variously reported as an intermediate to certain beta-lactam antibacterial agents (Sheehan, U.S. Pat. No. 2,721,197), as an antidepressant agent (Plotnikoff, U.S. Pat. No. 3,699,229) and as an anticonvulsant agent [Brink and Freeman, J. Neuro. Chem. 19 (7), pp. 1783–1788 (1972)]; a number of 5-phenyloxazolidine-2,4-diones substituted on the phenyl ring, e.g., 5-(4-methoxyphenyl)oxazolidine-2,4-dione [King and Clark-Lewis, J. Chem. Soc., pp. 3077–3079 (1961)], 5-(4-chlorophenyl)oxazolidine-2,4-dione [Najer et al., Bull. soc. chim. France, pp. 1226–1230 (1961)], 5-(4-methylphenyl)oxazolidine-2,4-dione [Reibsomer et al., J. Am. Chem. Soc. 61, pp. 3491–3493 (1939)], and 5-(4-aminophenyl)oxazolidine-2,4-dione (German Pat. No. 108,026); and 5-(2-pyrryl)oxazolidine-2,4-dione [Ciamacian and Silber, Gazz. chim. ital. 16, 357 (1886); Ber. 19, 1708–1714 (1886)]. The last-named compound, having no prior known utility, shows only relatively weak hypoglycemic activity (vide post, Table I).

Oxazolidine-2,4-dione and substituted oxazolidine-2,4-diones (specifically, the 5-methyl and 5,5-dimethyl derivatives) have been reported as acid moieties suitable for forming acid-addition salts with the hypoglycemic, basic biguanides (Shapiro and Freedman, U.S. Pat. No. 2,961,377). We have determined that neither oxazolidine-2,4-dione itself, nor 5,5-dimethyloxazolidine-2,4-dione possess the hypoglycemic activity of the compounds of the present invention.

Recently, a group of spiro-oxazolidine-2,4-dione derivatives have been reported which are aldose reductase inhibitors, thus finding utility in the treatment of certain complications of diabetes (Schnur, U.S. Pat. No. 4,200,642).

A process for the synthesis of 3-aryloxazolidine-2,4-diones (wherein said aryl group is 6 to 12 carbon atoms, unsubstituted or substituted with one or more halogen atoms, methyl or methoxy) is the subject of another recent U.S. Pat. No. (Scholz, U.S. Pat. No. 4,220,787). The utility of these compounds is not specified.

SUMMARY OF THE INVENTION

The present invention is concerned with compounds of the formula

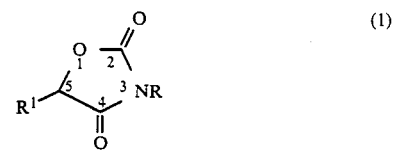

wherein

R is hydrogen, $(C_1-C_4)$-alkanoyl (e.g., formyl, acetyl, isobutyryl), benzoyl, $(C_2-C_4)$-carbalkoxy (e.g., carbomethoxy, carbethoxy, carboisopropoxy), $(C_1-C_3)$-alkylcarbamoyl (e.g., N-methylcarbamoyl, N-propylcarbamoyl), $(C_5-C_7)$-cycloalkylcarbamoyl (e.g., N-cyclohexylcarbamoyl) or di-$(C_1-C_3)$-dialkylcarbamoyl e.g., N,N-dimethylcarbamoyl); and $R^1$ is:

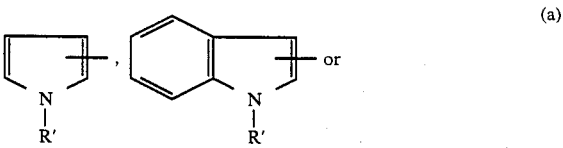

(a)

-continued

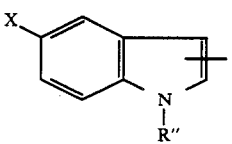

wherein R' is (C$_1$-C$_4$)alkyl or phenyl, R" is hydrogen, (C$_1$-C$_4$)alkyl or phenyl and X is halo (fluoro, chloro, bromo or iodo); these formulae are intended to emcompass 2- or 3-pyrrolyl and indolyl derivatives, with substituents as specified;

(b)

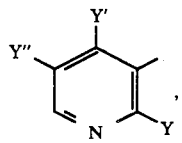

wherein Y is hydrogen or (C$_1$-C$_3$)alkoxy, Y' is hydrogen or (C$_1$-C$_3$)alkyl and Y" is hydrogen or halo;

(c)

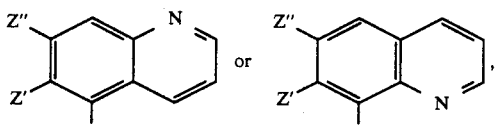

wherein Z' is hydrogen, halo or (C$_1$-C$_3$)alkoxy and Z" is hydrogen or halo;

(d)

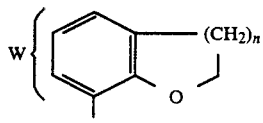

wherein W is hydrogen or halo, and n is 1 or 2; these formula are intended to encompass 6- or 7-halo-8-chromanyl or 5- or 6-halo-7-benzofuranyl derivatives;

(e)

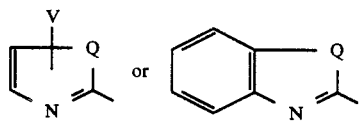

wherein Q is sulfur or oxygen and V is hydrogen or (C$_1$-C$_3$)alkyl; or (f)

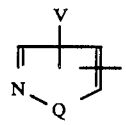

wherein Q is sulfur or oxygen; and V is hydrogen or (C$_1$-C$_3$)alkyl; these formula are intended to encompass 3-, 4- and 5-isothiazolyl and isoxazolyl derivatives; and pharmaceutically acceptable cationic salts thereof when R is hydrogen, as well as the pharmaceutically acceptable acid addition salts thereof when R$^1$ contains a basic nitrogen function.

It is believed that the inherent, high activity of these compounds resides primarily in those compounds wherein R is hydrogen, and that those compounds wherein R is one of a variety of carbonyl derivatives defined above represent so-called pro-drugs, i.e., the carbonyl side chain is removed by hydrolysis under physiological conditions, yielding the fully-active compounds wherein R is hydrogen.

The expression "pharmaceutically acceptable cationic salts" is intended to define such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc.

The expression "pharmaceutically acceptable acid addition salts" is intended to include such salts as the hydrochloride, hydrobromide, hydroiodide, nitrate, hydrogen sulfate, dihydrogen phosphate, mesylate, maleate, succinate, etc.

The compounds of the present invention possess hypoglycemic activity, reflecting their clinical utility in the lowering of the blood glucose level of hyperglycemic mammals, including man, to normal values. They have the special advantage of lowering blood glucose values to a normal range without danger of causing hypoglycemia. The compounds of the present invention are tested for hypoglycemic (anti-hyperglycemic) activity in rats, using the so-called glucose tolerance test, as described in greater detail hereinafter.

Preferred compounds, because of their better hypoglycemic activity, are those wherein R is hydrogen, or the pharmaceutically acceptable salts thereof. Among those compounds of the formula (1) wherein R is hydrogen, the most preferred compounds, because of their excellent hypoglycemic activity, are:
5-(1-methyl-2-pyrrolyl)oxazolidine-2,4-dione;
5-(1-ethyl-2-pyrrolyl)oxazolidine-2,4-dione;
5-(1-phenyl-2-pyrrolyl)oxazolidine-2,4-dione;
5-(2-methoxy-3-pyridyl)oxazolidine-2,4-dione;
5-(2-ethoxy-3-pyridyl)oxazolidine-2,4-dione;
5-(5-chloro-2-methoxy-3-pyridyl)oxazolidine-2,4-dione;
5-(5-chloro-2-ethoxy-3-pyridyl)oxazolidine-2,4-dione;
5-(8-quinolyl)oxazolidine-2,4-dione;
5-(7-methoxy-8-quinolyl)oxazolidine-2,4-dione;
5-(6-chloro-8-quinolyl)oxazolidine-2,4-dione;
5-(6-fluoro-8-quinolyl)oxazolidine-2,4-dione;
5-(2-benzthiazolyl)oxazolidine-2,4-dione;
5-(2-thiazolyl)oxazolidine-2,4-dione;
5-(6-chloro-8-chromanyl)oxazolidine-2,4-dione;
5-(6-fluoro-8-chromanyl)oxazolidine-2,4-dione;
5-(5-chloro-2,3-dihydro-7-benzofuranyl)oxazolidine-2,4-dione; and
5-(3-methyl-5-isoxazolyl)oxazolidine-2,4-dione.

DETAILS OF THE INVENTION

The compounds of the present invention are prepared by a variety of methods, as summarized in Flowsheet I, wherein
R$^1$ is as defined above;
R$^2$ is lower alkyl (e.g. methyl or ethyl);
R$^3$ is hydrogen, lower alkyl or phenyl; and
R$^4$ is hydrogen, or acyl such as acetyl or benzoyl.

A particularly convenient synthesis for compounds of the present invention is via carboximidate (3). The latter compound is reacted with phosgene in an inert solvent such as tetrahydrofuran in the presence of 2 to 2.3 equivalents of a tertiary amine (e.g. triethylamine, N-methylmorpholine). A further equivalent of tertiary amine is used if the carboximidate is introduced as the acid addition salt (e.g. hydrochloride salt). The temperature of the reaction is not critical, but lower temperatures (e.g. −10° to 10° C.) are preferred during the initial stages of the reaction, particularly if it is desired to isolate the intermediate 4-alkoxyoxazol-2-one (4). Isolation of this intermediate is carried out by simple evaporation of the reaction mixture to dryness. On further reaction at higher temperatures (e.g. 20°–150° C.) or on aqueous work-up the intermediate (4) is converted to the desired oxazolidine-2,4-dione. When a primary or secondary amine function is desired in the final product, this functionality is introduced via an oxazolidine-2,4-dione containing a group selectively reducible (e.g. by catalytic hydrogenation or acid/metal couple) to the primary or secondary amine. For example an N-benzylindole can be used as a precursor for an indole derivative.

Flowsheet I
Oxazolidine-2,4-dione Precursors

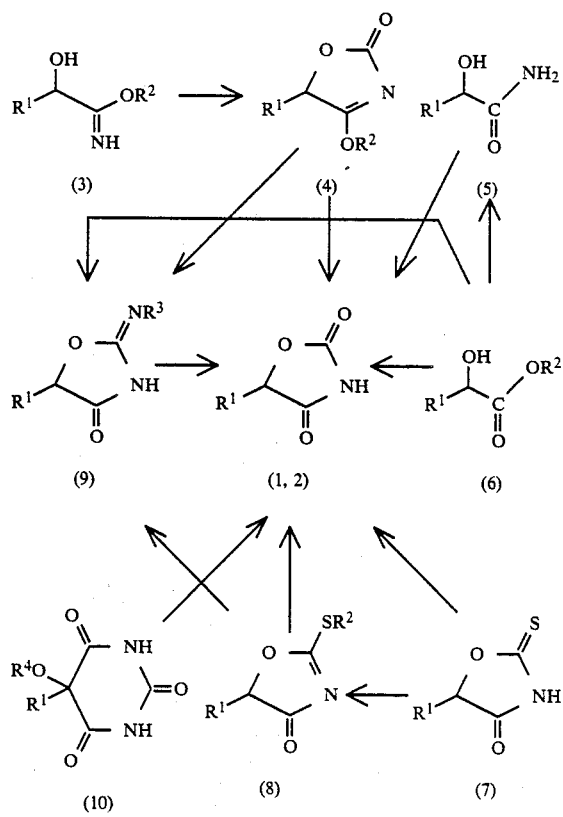

The carboximidate (3) is conveniently prepared from the corresponding aldehyde by the sequence:

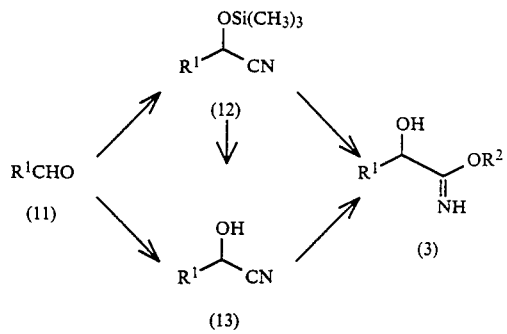

The aldehyde (11) is converted to the cyanohydrin (13) by standard procedures (e.g. via the bisulfite adduct, which is reacted with cyanide in a two phase, aqueous-organic solvent system). Alternatively, the aldehyde is converted to the trimethylsilyl cyanohydrin (12) by reaction with trimethylsilylcarbonitrile in the presence of a catalytic quantity of a Lewis acid, e.g., zinc iodide. A reaction inert solvent (e.g. methylene chloride, ether) is generally used when the aldehyde is a solid, but is optional when the aldehyde is a liquid. The temperature of the reaction is not critical, it being conveniently made up at reduced temperature (e.g. 0°–5° C.) and allowed to proceed at room temperature for a matter of hours or days, as necessary to achieve complete reaction. If desired, the trimethylsilyl ether can be hydrolyzed to cyanohydrin, conveniently at reduced temperature (e.g. −10° C.) in a two phase strong aqueous acid/organic solvent system.

Either the cyanohydrin (13) or the trimethylsilyl ether (12) is converted to the carboximidate (3) by strong acid catalyzed alcoholysis (using strictly anhydrous conditions). A convenient method is to simply dissolve the nitrile in alcohol which has been saturated with hydrogen chloride) and allow the solution to stand until carboximidate formation is complete. Temperature is not critical, although lower temperatures (e.g. 0°–25° C.) generally lead to more optimal yields.

The aldehydes required for the above syntheses are broadly available either commercially, or by literature methods. For example, N-alkylpyrrole-2-carbaldehydes are obtained by alkylation of pyrrole-2carbaldehyde (Weygand, Organic Preparations, Interscience, New York, 1945, p. 403) using conditions specifically exemplified hereinafter for the preparation of N-alkylpyrroles, or by Reimer-Tieman formylation of N-alkylpyrrole (cf Weygand loc. cit.); 3-formylindoles are similarly obtained from indoles [cf Boyd and Robson, Biochem J. 29, p. 555 (1935; Shabica et al., J. Am. Chem. Soc. 68, p. 1156 (1946)]; a variety of the presently required aldehydes are further available by the Rosenmund reduction of the corresponding acid chlorides, the hydrolysis of gem-dihalides, oxidation of primary alcohols, interaction of Grignard reagents with orthoformic esters and other methods known in the art. Additional methods are noted in the Preparations detailed hereinafter.

Another suitable precursor for those oxazolidine-2,4-diones of the present invention lacking a primary or secondary amine function is the alpha-hydroxy amide (5). The latter compound is converted to the desired oxazolidine-2,4-dione (1), either by reaction with alkyl chloroformate in the presence of a basic catalyst such as potassium carbonate, or by reaction with a dialkyl carbonate in the presence of a more strongly basic catalyst such as sodium methoxide or potassium tert-butoxide. An alcohol is generally suitable as solvent for the latter reaction with 1 to 3 equivalents of both dialkyl carbonate and base employed, preferably 2-3 equivalents of each. When a primary or secondary amine function is desired in the final product, this functionality is introduced via an oxazolidine-2,4dione containing a suitable precursor group, as described above.

The required alpha-hydroxy amide is conveniently prepared from cyanohydrin (13) or from alpha-hydroxy acid or ester (6):

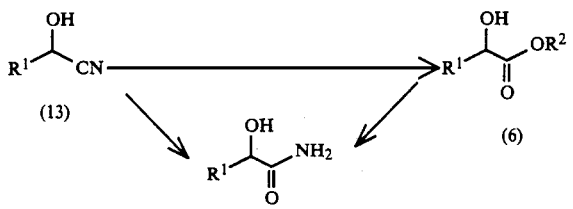

Convenient conditions for the hydrolysis of the cyanohydrin (13) are to treat the cyanohydrin in formic acid with excess concentrated hydrochloric acid. A temperature range of 0°-75° C. is generally satisfactory, depending upon the stability of the individual amide in this medium. If desired, an intermediate formate ester of (5) can be isolated under these conditions. Over hydrolysis to the acid can be avoided by tlc monitoring of the reaction, as detailed below. Convenient conditions for the aminolysis of ester (6) are to simply heat the ester in hot concentrated ammonium hydroxide.

The alpha-hydroxy ester (6) itself can also be employed as the immediate precursor of the desired oxazolidine-2,4-dione. The ester is reacted with urea (or one of certain substituted ureas, such as phenyl urea or 1-acetyl-3-methylurea) in the presence of a basic catalyst such as sodium ethoxide (suitably 1 equivalent) in alcohol at a temperature of 50°-110° C. The ester to be used for this purpose is by no means restricted to a simple lower alkyl ester, but can be any one of a broad variety of esters, e.g. phenyl, benzyl, etc. Furthermore, the ester can be replaced by a 1,3-dioxolan-4-one, an alpha-acyloxy ester or a thioester e.g.,

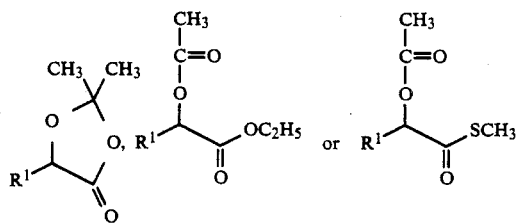

and the urea can be replaced by a urethan.

Two other precursors suitable for the synthesis of the desired oxazolidine-2,4-diones are the thio compounds (7) and (8). The 2-thioxo compound (7) is converted to the desired oxazolidine-2,4-diones under oxidative conditions, e.g. mercuric ion, aqueous bromine or chlorine, metaperiodate, or aqueous hydrogen peroxide, usually in excess and in the presence of a cosolvent, such as a lower alcohol. The temperature of reaction is not critical, temperatures in the range 25°-100° C. being generally satisfactory. Other methods are usually preferred when $R^1$ has an amine function, since competing oxidation at the nitrogen tends to reduce yields and complicates isolation of the desired product; it has been found, however, that when the product contains a tert-amine (e.g., pyridine, quinoline), that periodate or bromine are reagents well-suited for this purpose. The oxazolidine-2,4-diones are obtained from the alkylthio compounds (8) by simple acid or base catalyzed hydrolysis. Preferable conditions are aqueous hydrochloric acid in a temperature range of 0°-50° C.

The precursor 2-thioxo compound (7) is prepared from the corresponding aldehyde (11), generally accomplished in an aqueous acidic media by the action of thiocyanate (1–1.1 equivalents) and cyanide (1 to 1.2 equivalents) at 0°-70° C., following the method of Lindberg and Pederson by which method the preparation of 5-(2-thienyl)-2-thiooxazolidin-4-one has been reported [Acta Pharm. Suecica 5 (1), pp. 15–22 (1968); Chem. Abstr. 69, 52050k]. The precursor 2-alkylthio compounds (8) can be prepared by alkylation of the 2-thioxo compounds (7), e.g. with an alkyl halide or dialkyl sulfate, preferably in the presence of at least two equivalents of a base such as a lower alkoxide in a reaction inert solvent such as a lower alkanol. The 3-alkyl derivative can be a by-product of this reaction.

Also suitable as a precuror is the 2-imino-oxazolidine-4-one derivative (9), readily hydrolyzed to the oxazolidine-2,4-dione, preferably under aqueous acid conditions. The required 2-iminooxazolidin-4-one is obtained by condensation of the alpha-hydroxy ester (6) with guanidine or with thiourea in the presence of one equivalent of a strong base such as sodium alkoxide, by ammonolysis of the 2-alkoxy compound (isomeric with 4) or the 2-thioalkyl compound (8), by alkali induced cyclization of the appropriate alpha-halogenureides ($R^1CHZCONHCONHR^3$ wherein Z is a halogen such as chloro or bromo), or by the condensation of the appropriate alkyl alpha-haloacetates ($R^1CHZCOOR^2$) with urea or a substituted urea ($R^3NHCONH_2$).

Ammonolysis of the 4-alkoxy derivatives (4) yields 4-imino derivatives (isomeric with 9). The latter compounds are also readily hydrolyzed to oxazolidine-2,4-diones. The 4-alkoxy derivatives themselves are also prepared from the silver salt of the desired oxazolidine-2,4-dione.

Also highly useful as precursors of the oxazolidine-2,4-diones of the present invention are the dialuric acids and acyl dialuric acids (10). These are readily converted, under mildly basic conditions, to the desired oxazolidine-2,4-diones. Methods suitable for the preparation of precursor dialuric acids (10) are shown in Flowsheet II, wherein the substituents $R^1$, $R^2$ and $R^4$ are as defined above, and M is Li, MgCl, MgBr, MgI, or other suitable metal.

A general method for preparing dialuric acids appropriate as precursors of the oxazolidine-2,4-diones of the present invention is from the malonic ester derivatives (14), involving the two stages of base catalyzed condensation with urea and oxidation to the hydroxy or acyloxy compound. When the first stage is oxidation, the intermediate is a so-called tartronic acid derivative (15), while when the first stage is condensation, the intermediate is a so-called barbituric acid (16). When $R^1$ contains an amine function (e.g. 2-aminophenyl), it is preferred to carry out oxidation as the first stage, preventing possible complications of nitrogen oxidation. When condensation is the second stage, the dialuric acid is usually not isolated, at least in pure form, and is further converted, under basic conditions of the condensation, to the oxazolidine-2,4-dione.

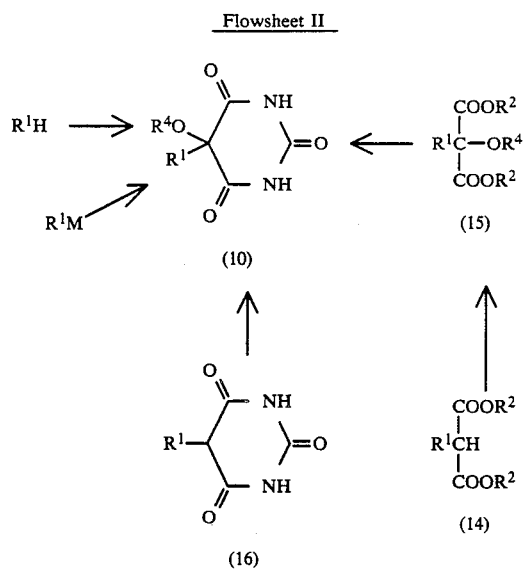

Flowsheet II

The substituted malonic esters required for the above syntheses, when not available commercially, are obtained by literature methods, such as alcoholysis of alpha-cyano esters [cf. Steele, J. Am. Chem. Soc. 53, (1931)], carbalkoxylation of esters [cf. Horning and Finelli, Org. Syntheses 30, 43 (1950)]and decarbonylation of alpha-keto esters obtained by the condensation of dialkyl oxalate with carboxylate esters [Reichstein and Morsman, Helv. Chim. Acta 17, (1934); Blicke and Zienty, J. Am Chem. Soc. 63, (1941)].

A less general method for the preparation of the appropriate dialuric acid intermediate is to react an electron rich heteroaryl/aryl compound, e.g.,

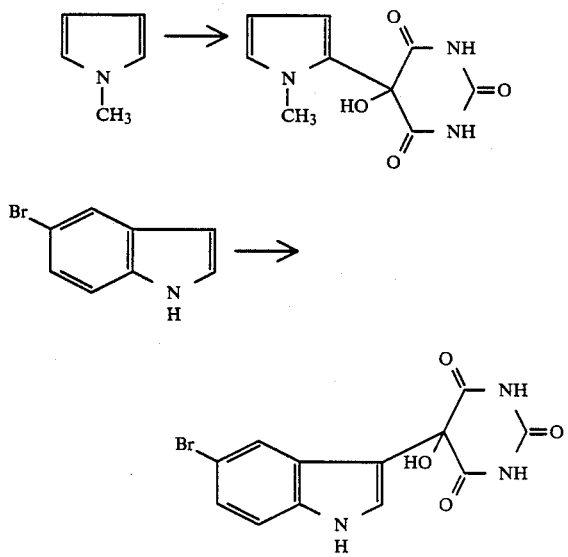

Now available is yet another method for the preparation of certain dialuric acid intermediates. This method, preferred when the appropriate starting materials are readily available, involves the reaction of alloxan (preferably in anhydrous form) with the appropriate organo-metal derivative (e.g., organolithium, Grignard reagent). For example:

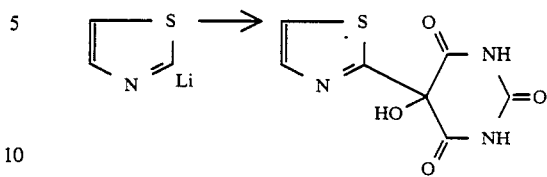

Protection strategies are required when using this method for preparation of certain oxazolidine-2,4-diones wherein $R^1$ carries a substituent which is not compatible with organometallic reactions, e.g., an acyl group is protected as its ethylenic ketal. In other cases, such as when $R^1$ carries a group such as nitro or amino, this method generally lacks utility.

It will be evident to those skilled in the art that the preferred process for the oxazolidine-2,4-diones of the present invention will vary from one given value of $R^1$ to another, depending upon such factors as availability of starting materials, yields, ability to remove undesirable impurities from the end-products, the chemical nature of the substituent groups contained in the final products, etc.

The pharmaceutically-acceptable cationic salts of the compounds of the present invention which form such salts are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. Those salts which do not precipitate directly are isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

The pharmaceutically acceptable acid addition salts of the compounds of the present invention which form such salts are readily prepared by reacting the base forms with an appropriate acid, usually one equivalent, in a cosolvent. Typical acids are hydrochloric, hydrobromic, nitric, sulfuric, phosphoric, methanesulfonic, maleic, succinic, etc. Those salts which do not precipitate directly are isolated by concentration to dryness or by addition of a non-solvent.

3-Acylated derivatives of the present invention are readily prepared by using standard conditions of acylation, e.g. the reaction of the oxazolidine-2,4-dione salt (per se, or conveniently formed in situ by the addition of one equivalent of a tertiary amine such as triethylamine or N-methylmorpholine with an equivalent of the appropriate acid chloride or acid anhydride) or reaction of the oxazolidine-2,4-dione with the appropriate organic isocyanate, optionally in the presence of a catalytic amount of tertiary amine base. In either case, the reaction is carried out in a reaction inert solvent, such as toluene, tetrahydrofuran or methylene chloride. The temperature is not critical, and can be over a broad range (e.g. 0°–150° C.). It will be evident to those skilled in the art that such acylation will be complicated by competing or even selective sidechain (R¹) acylation when the sidechain contains a primary or secondary amine function.

It will be evident to those skilled in the art that the compounds of the present invention are asymmetric and therefore capable of existing in two optically active enantiomeric forms. The racemic compounds of the present invention, being acids when R is H, form salts with organic amines. These racemic forms are therefore generally capable of resolution into the optically active forms by the classic method of forming diastereomeric salts with optically active amines, now separable by selective crystallization; alternatively those compounds containing a basic amine function can be resolved by forming a salt with an optically active acid, preferably a strong organic acid such as a sulfonic acid. In general, one of the enantiomeric forms is found to have greater activity than the other.

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

The oxazolidine-2,4-diones of the present invention are readily adapted to clinical use as antidiabetic agents. The hypoglycemic activity required for this clinical use is defined by the glucose tolerance test procedure which follows. Intact male albino rats are the experimental test animals employed for such purposes. The test animals are fasted approximately 18-24 hours. The rats are weighed, numbered and recorded in groups of five or six as needed. Each group of animals is then dosed intraperitoneally with glucose (one gram per kilogram) and orally with either water (controls) or compound (at a level usually selected from the range 0.1 to 100 mg/kg). Blood glucose levels (mg/100 ml.) are measured in tail blood samples over a period of 3 hours in both control and treated groups. With equivalent zero hour blood glucose levels in control and treated groups, the % lowering of blood glucose at 0.5 hour, 1 hour, 2 hours and 3 hours is calculated as:

$$\frac{[\text{Control Blood Glucose}] - [\text{Treated Blood Glucose}]}{[\text{Control Blood Glucose}]} \times 100\%$$

Clinically useful hypoglycemic agents show activity in this test. The hypoglycemic activities determined for compounds of the present invention are summarized in Table I. This table records % blood gluose lowering at the 0.5 hour and 1 hour time points. A blood glucose lowering of 9% or greater generally reflects statistically significant hypoglycemic activity in this test. Those compounds which show significant activity only at the 2 hour or 3 hour points have such activity recorded in footnotes.

TABLE I

Hypoglycemic Activity of Oxazolidine-2,4-Diones in the Rat Glucose Tolerance Test

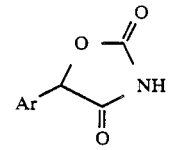

| Ar | Dose (mg./kg.) | % Lowering of Blood Glucose Level 0.5 hr. | 1 hr. |
|---|---|---|---|
| 8-Chromanyl | — | — | — |
| 6-Chloro- | 10 | — | 11 |
| 6-Fluoro- | 10 | — | 9 |
| 2,3-Dihydrobenzofuranyl | — | — | — |
| 5-Chloro- | 25 | — | 23[a] |
| 2-Pyrrolyl | 100 | 11 | 8 |
| 1-Methyl- | 100 | 18 | 17 |
| 1-Ethyl- | 100 | 14 | 16 |
| 1-(1-Butyl)- | 100 | 4 | 13 |
| 1-Phenyl | 100 | 30 | 32 |
| 3-Indolyl | — | — | — |
| 5-Bromo- | 100 | 9 | 10 |
| 1-Methyl- | 100 | 11 | 8 |
| 3-Pyridyl | — | — | — |
| 2-Methoxy- | 10 | — | 13 |
| 2-Ethoxy- | 25 | — | 20 |
| 2-Methoxy-5-chloro- | 25 | 22 | 17 |
| 2-Ethoxy-5-chloro- | 10 | — | 24[a] |
| 5-Quinolyl | — | — | — |
| 6-Methoxy- | 20 | — | 7[b] |
| 8-Quinolyl | 18 | 19 | 16 |
| 6-Chloro- | 10 | — | 16 |
| 6-Fluoro- | 10 | — | 15 |
| 7-Methoxy- | 10 | — | —[c] |
| 2-Thiazolyl- | 75 | 11 | 10 |
| 2-Benzthiazolyl- | 50 | 8 | 10 |
| 5-isoxazolyl | — | — | — |
| 3-Methyl- | 100 | 4 | 7[d] |

[a] At 0.75 hour.
[b] 9 at 2 hours.
[c] 12 at 3 hours.
[d] 24 at 2 hours, 14 at 3 hours.

The oxazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg. body weight of the subject per day, preferably about 0.20 to about 20 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions can if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intramuscular administration being preferred in man.

The present invention is illustrated by the following examples. However, it should be understood that the invention is not limited to the specific details of these examples.

EXAMPLE 1

Methyl 2-Methoxypyridine-3-carboxylate

Thionyl chloride (50 ml.) was added to 2-methoxypyridine-3-carboxylic acid (5 g.) in 50 ml. of carbon tetrachloride and the mixture refluxed for 2 hours. The reaction mixture was cooled, evaporated to solids and chased with multiple portions of fresh carbon tetrachloride. The resulting acid chloride hydrochloride was dissolved in excess methanol (50 ml.), stirred for 16 hours at room temperature, then evaporated an oil and taken up in chloroform. The chloroform solution was washed with two portions of saturated sodium bicarbonate and then one portion of brine, dried over anhydrous magnesium sulfate, filtered and evaporated to yield title product as an oil [4.63 g.; pnmr/CDCl$_3$/delta (ppm): 3.9 and 4.1 (2s, 6H), 6.9 (m, 1H), 8.2 (m, 2H)].

By the same procedure, 4-methylpyridine-3-carboxylic acid is converted to methyl 4-methylpyridine-3-carboxylate.

EXAMPLE 2

3-Methanesulfinylmethylcarbonyl-2-Methoxypyridine

Sodium hydride (2.69 g., 50% dispersion in oil, 0.056 mole) was washed three times with petroleum ether. Following the third decantation, traces of petroleum ether were removed by evaporation in vacuo. Dimethylsulfoxide (30 ml.) was added and the mixture heated in an oil bath at 75° C. for 45 minutes, by which time hydrogen evolution had ceased. The mixture was cooled in an ice-water bath and diluted with 30 ml. of dry tetrahydrofuran. Title compound of the preceding Example (4.63 g., 0.028 mole) in 10 ml. of dry tetrahydrofuran was added dropwise over 5 minutes. The reaction mixture was warmed and stirred at room temperature for 30 minutes, poured into 180 ml. of water, acidified to pH 4 with 1N hydrochloric acid and extracted with three portions of chloroform. The combined organic layers were dried over magnesium sulfate, filtered and concentrated to yield title product as an oil [4.97 g.; pnmr/CDCl$_3$/delta (ppm); 2.8 (s, 3H), 4.1 (s, 3H), 4.4 and 4.7 (2d, 2H), 7.0 (m, 1H), 8.3 (m, 2H)].

By the same procedure the 4-methyl compound of the preceding Example is converted to 3-methanesulfinylmethylcarbonyl-4-methylpyridine.

EXAMPLE 3

S-Methyl 2-Acetoxy-2-(2-methoxy-3-pyridyl)thioacetate

Title compound of the preceding Example (3.97 g.), sodium acetate (3.97 g.) and acetic anhydride (40 ml.) were combined in 80 ml. of toluene and heated at 115° for 16 hours. The mixture was cooled and evaporated to dryness in vacuo to yield crude product. The latter was chromatographed on 200 g. of silica gel with 2:1 chloroform:ethyl acetate as eluant, tlc monitoring and collecting 10 ml. fractions. Clean product fractions 58–79 were combined and concentrated to an oil. To remove possible traces of residual acetic anhydride, the oil was taken into wet ethanol, held for 15 minutes, re-evaporated, chased with toluene, taken up in chloroform, dried over anhydrous magnesium sulfate, filtered, and re-evaporated to yield the title product as an oil [3.16 g.; Rf 0.60 (3:1 ethyl acetate: methanol); m/e 255; ir (CH$_2$Cl$_2$) 1748, 1686, 1582, 1460, 1205 cm$^{-1}$].

By the same procedure the methyl compound of the preceding Example is converted to S-methyl 2-acetoxy-2-(4-methyl-3-pyridyl)thioacetate.

EXAMPLE 4

5-(2-Methoxy-3-pyridyl)oxazolidine-2,4-dione

Sodium methoxide (632 mg., 11.7 mmoles) was taken into 50 ml. of absolute ethanol and the solution cooled in an ice-water bath. Urea (234 mg., 3.9 mmole) was added, followed by the title compound of the preceding Example (1.0 g., 3.9 mmole) in 5 ml. of ethanol. The mixture was heated at reflux for 16 hours, then cooled to room temperature, neutralized with 11.7 ml. of 1N hydrochloric acid and evaporated to a gum which was chased with toluene. The gum was chromatographed on 40 g. of silica gel with 1:2 ethyl acetate:chloroform as eluant, tlc monitoring and 10 ml. fractions collected. Product containing fractions 6–15 were combined and evaporated to a viscous oil, which was crystallized from water [75 mg; m.p. 183°–186° C., Rf 0.32 (1:2 ethyl acetate:chloroform)].

By the same method, the methyl analog of the preceding Example is converted to 5-(4-methyl-3-pyridyl)oxazolidine-2,4-dione.

EXAMPLE 5

Ethyl 2-Ethoxypyridine-3-carboxylate

2-Ethoxypyridine-3-carboxylic acid (4 g.) was converted to its acid chloride hydrochloride by refluxing with 8.6 ml. of thionyl chloride for 60 minutes. The reaction mixture was evaporated to solids with toluene chase to removed the excess thionyl chloride. The residue was taken into 80 ml. of ethanol and held for 16 hours at 0° C., then evaporated to solids, which were partitioned between toluene and 1N sodium hydroxide. The aqueous layer was extracted with fresh toluene and the two organic layers combined, washed with water and then brine, dried over anhydrous magnesium sulfate, filtered and evaporated to yield title product as an oil [3.2 g.; pnmr/CDCl$_3$/delta (ppm) 1.6 (2s, 6H), 4.4–5.0 (2q, 4H), 7.2 and 8.2 (m, 3H)].

EXAMPLE 6

2-Ethoxy-3-methanesulfinylmethyl carbonylpyridine

Using methylene chloride in place of chloroform in the isolation, the procedure of Example 2 was employed to convert product of the preceding Example (3.0 g.) to title product [2.63 g.; m.p. 89°–91° C.; pnmr/CDCl$_3$/delta (ppm), 1.5 (t, 3H),22.8 (s, 3H), 4.2–4.8 (s and q, 4H), 6.8–7.1 and 8.0–8.4 (3H)].

EXAMPLE 7

S-Methyl 2-Acetoxy-2-(2-ethoxy-3-pyridyl)-thioacetate

Using a reaction time of 4 hours at 100° C. and then 48 hours at room temperature, the procedure of Example 3 was employed to convert the product of the preceding Example (2.5 g.) to crude product, isolated as an oil by evaporation of the reaction mixture. The oil was taken up in ethyl acetate, washed in sequence with three portions of 1N sodium hydroxide, one of water and one of brine, dried over anhydrous magnesium sulfate and evaporated to yield title product as an oil [2.96 g.; Rf 0.78 (10:1 ethyl acetate:methanol); m/e 269].

EXAMPLE 8

2-(2-Ethoxy-3-pyridyl)-2-hydroxyacetamide

Product of the preceding Example (2.9 g.) was combined with 30 ml. of ethanol and 30 ml. of conc. ammonium hydroxide, stirred at room temperature for 3 hours and then evaporated to yield crude product as an oil (2.7 g.). The oil was chromatographed on 170 g. of silica gel using ethyl acetate as eluant and tlc monitoring. Clean product fractions were combined and evaporated to yield title product as an oil [0.9 g.; Rf 0.6 (10:1 ethyl acetate:methanol); pnmr/CDCl$_3$/delta (ppm) 1.4 (t, 3H), 4.5 (q, 2H), 5.4 (s, 1H), 6.2–8.2 (m, 5H)].

EXAMPLE 9

5-(2-Ethoxy-3-pyridyl)oxazolidine-2,4-dione

Product of the preceding Example (900 mg., 4.6 mmole) was combined with 25 ml. of tert-butanol. Dimethyl carbonate (1.08 g., 9.2 mmole) and then potassium tert-butoxide (1.03 g., 9.2 mmole) were added and the reaction mixture refluxed for 3.5 hours. The reaction mixture was cooled, poured into 10 ml. of 1N hydrochloric hydrochloric acid, the pH adjusted to 7.0, and extracted with two portions of ethyl acetate. The aqueous layer was saturated with salt and extracted with additional ethyl acetate. The three organic layers were combined, back-washed with a small portion of water and then brine, dried over anhydrous magnesium sulfate and evaporated to yield crude product as a viscous oil. Purified title product was obtained by crystallization from toluene (295 mg., m.p. 140°–143° C.; m/e 272).

Anal. Calcd. for: $C_{10}H_{10}O_4N_2$:
C, 54.05; H, 4.54; N, 12.61.
Found: C, 54.34, H, 4.85, N, 12.70.

EXAMPLE 10

Methyl 5-Chloro-2-methoxypyridine-3-carboxylate

By the procedure of Example 1, 5-chloro-2-methoxypyridine-3-carboxylic acid [Sarges et al., J. Med. Chem. 19, 709 (1976); 10 g.] was converted to its acid chloride, which was added in one portion to 150 ml. of methanol (slight exotherm), then made basic with triethylamine (approximately 1.1 equivalents). The reaction mixture was evaporated to solids and the residue partitioned between ethyl acetate and water. The ethyl acetate layer was washed with fresh water and then brine, dried over anhydrous magnesium sulfate, filtered and evaporated to yield title product [9.75 g., m.p. 79°–81° C.; pnmr/CDCl$_3$/delta (ppm) 3.8 (s, 3H), 4.1 (s, 3H), 8.1 (d, 1H), 8.3 (d, 1H)].

EXAMPLE 11

5-Chloro-3-methanesulfinylmethylcarbonyl-2-methoxypyridine

By the procedure of Example 2, the product of the preceding Example (9.7 g., 0.045 mole) was converted to title product isolated as a visous oil (10.3 g., m/e 249/247).

EXAMPLE 12

S-Methyl 2-Acetoxy-2-(5-chloro-2-methoxy-3-pyridyl)thioacetate

Using a reaction time of 19 hours at 100° C., the procedure of Example 3 and the isolation method of Example 7 were employed to convert product of the preceding Example (10.3 g.) to title product in the form of a viscous oil (8.8 g.; pnmr/CDCl$_3$ includes singlet at 6.4; m/e 291/289).

EXAMPLE 13

2-(5-Chloro-2-methoxy-3-pyridyl)-2-hydroxyacetamide

Methanol (125 ml.) was saturated with anhydrous ammonia at 0°–5° C. The product of the preceding Example (8.8 g.) in 25 ml. of methanol was added and the reaction mixture stirred overnight at room temperature, then concentrated to a viscous oil (7.3 g.). The oil was chromatographed on 400 g. of silica gel using 1:1 chloroform:ethyl acetate as eluant, tlc monitoring and 10 ml. fractions. Clean product fractions 190–270 were combined and evaporated to yield title product [1.3 g.; m.p. 110°–113° C.; m/e 218/216; ir(KBr) 3444, 3410, 1684 cm$^{-1}$].

EXAMPLE 14

5-(5-Chloro-2-methoxy-3-pyridyl)oxazolidine-2,4-dione

Using a reflux period of 15 hours, the procedure of Example 9 was employed to convert the product of the preceding Example (1.25 g., 5.8 mmoles) to title product. To isolate, the reaction mixture was cooled to room temperature and the pH adjusted to 3 with 1N hydrochloric acid. The mixture was then evaporated in vacuo to slightly gummy solids, which gave filterable, crude product on stirring with 25 ml. of water (1.09 g., m.p. 199°–204° C. Recrystallization from 15 ml. of ethanol gave purified title product [470 mg.; m.p. 212°–214° C.; m/e 244/242; ir(KBr) 3174, 3074, 2980, 1830, 1752 cm$^{-1}$].

EXAMPLE 15

2-(6-Chloro-8-quinolyl)-2-hydroxyacetamide

Ethyl 2-(6-chloro-8-quinolyl)-2-hydroxyacetate (1.6 g.) in 300 ml. of conc. ammonium hydroxide was heated to reflux. Since complete dissolution did not result, the reaction mixture was cooled, diluted with 50 ml. of ethanol and reheated to reflux for 0.5 hour. The reaction mixture was concentrted to a volume of 100 ml., cooled slowly and a crop of title product (320 mg., m.p. 195°–198° C.) recovered by filtration. Additional product (145 mg). was recovered by concentration of the mother liquor to 50 ml. and extraction into three portions of ethyl acetate. The combined organic layers were washed with saturated sodium bicarbonate, dried over anhydrous magnesium sulfate, filtered and evaporated to dryness.

By the same procedure, ethyl 2-(6-chloro-2,3-dihydro-7-benzo[b]furanyl)-2-hydrxyacetate is converted to ethyl 2-(6-chloro-2,3-dihydro-7-benzo[b]furanyl)-2-hydroxyacetamide.

EXAMPLE 16

5-(6-Chloro-8-quinolyl)oxazolidine-2,4-dione

Potassium tert-butoxide (292 mg., 2.6 mmoles) was dissolved in 20 ml. of tert-butanol. Dimethyl carbonate (234 mg. 2.6 mmoles) and then title compound of the preceding Example (300 mg., 1.3 mmoles) were added. The reaction mixture refluxed for 18 hours, then cooled to room temperature, adjusted to pH 3 with 1N hydrochloric acid and diluted with 1N hydrochloric acid and ethyl acetate. The aqueous layer was washed with two additional portions of ethyl acetate. The organic layers were combined, washed with two portions of fresh 1N hydrochloric acid and then brine, dried over anhydrous magnesium sulfate, filtered and evaporated to an oil (130 mg.). Crystallization of the oil from isopropyl ether gave purified title product [58 mg., m.p. 207°–210° C.; ir(KBr) 1839, 1825, 1740 cm$^{-1}$].

By the same procedure the benzofuran analog of the preceding Example is converted to 5-(6-chloro-2,3-dihydro-7-benzo[b]furanyl)oxazolidine-2,4-dione.

EXAMPLE 17

2-(6-Fluoro-8-quinolyl)-2-hydroxyacetamide

Ethyl 2-(6-fluoro-8-quinolyl)-2-hydroxyacetate (1.1 g.) was refluxed for 10 minutes in 300 ml. of conc. ammonium hydroxide. The reaction mixture was cooled slightly, clarified by filtration and evaporated to solids. Trituration of the residue with 25 ml. of toluene gave the title product (860 mg., m.p. 169°–171° C.).

EXAMPLE 18

5-(6-Fluoro-8-quinolyl)oxazolidine-2,4-dione

Using a reflux period of 3.5 hours, the product of the preceding Example (840 mg., 3.8 mmoles) was converted to title product by the procedure of Example 16. In this case, a pH of 2 was used in the isolation without addition of excess 1N hydrochloric acid and the crude product was recrystallized from toluene [120 mg., m.p. 202°–204° C.; m/e 246; ir(KBr) 1819, 1743, 1363 cm$^{-1}$].

EXAMPLE 19

5-(8-Quinolyl)oxazolidin-4-one-2-thione

Potassium thiocyanate (484 mg., 4.9 mmoles) and potassium cyanide (370 mg., 5.7 mmoles) were combined in 5 ml. of water and cooled to 0° C. Quinoline-8-carbaldehyde [J. Org. Chem. 41, p. 957 (1976); 779 mg., 4.9 mmoles]was added, followed by the dropwise addition of hydrochloric acid (30%, 1.9 ml.). After stirring for 25 minutes at 0° C., the reaction mixture was heated to 90°–100° C. for 25 minutes, cooled, quenched into crushed ice, adjusted to pH 8 with sodium bicarbonate and extracted with cloroform. The organic layer was dried over anhydrous magnesium sulfate, filtered and evaporated to dryness (163 mg.). The latter was partitioned between 1N sodium hydroxide and ethyl acetate. The basic layer was acidified and extracted with fresh ethyl acetate. The two ethyl acetate layers were combined, dried, filtered and evaporated to yield title product [72 mg.; Rf 0.65 (ethyl acetate)]. The original, pH 8 aqueous layer was salted and extracted with ethyl acetate to yield an additional crop (114 mg.). The last aqueous phase was acidified and extracted with ethyl acetate to yield a third crop (115 mg.).

By the same method, 7-chloroquinoline-8-carbaldehyde is converted to 5-(7-chloro-8-quinolyl)oxazolidin-4-one-2-thione.

EXAMPLE 20

5-(8-Quinolyl)oxazolidine-2,4-dione

Title compound of the preceding Example (230 mg., 0.94 mmole) was taken into 6 ml. of 2:1 methanol:water and cooled to 0° C. Bromine (0.07 ml., 21.7 mg., 2.7 mmoles) was added and the reaction mixture allowed to warm slowly to room temperature, then stirred for 1 hour. The reaction mixture was evaporated to dryness and the residue partitioned between 1N sodium hydroxide and ethyl acetate. The aqueous layer was separated, acidified and extracted with two portions of fresh ethyl acetate. The acidic extracts were combined, dried and evaporated to an oil (144 mg.). Crystallization from toluene-chloroform and recrystallization from toluene gave purified title product (40 mg., m/e 228).

Anal. Calcd. for: Cl$_{12}$H$_8$O$_3$N$_2$·0.33H$_2$O:
C, 61.54; H, 3.70; N, 11.96.
Found: C, 61.50; H, 3.89; N, 11.52.

By the same method the chloro compound of the preceding Example is converted to 5-(7-chloro-8-quinolyl)oxazolidine-2,4-dione.

EXAMPLE 21

5-(6-Methoxy-5-quinolyl)oxazolidin-4-one-2-thione

By the procedure of Example 19, 6-methoxyquinoline-5-carbaldehyde (0.77 g.) was converted to title product. After quenching into ice, a first crop (190 mg.) was isolated by extraction into ethyl acetate, drying over anhydrous magnesium sulfate and evaporation to dryness. A second crop (176 mg.) was isolated in like manner by adjusting the aqueous phase to pH 8 with bicarbonate and extracting with additional ethyl acetate. Both crops had m/e 274. The second crop also had m/e 258, indicating contamination with the product of the next step.

EXAMPLE 22

5-(6-Methoxy-5-quinolyl)oxazolidine-2,4-dione

The combined product crops of the preceding Example (0.36 g., 1.31 mmole) were taken into 15 ml. of methanol. Sodium metaperiodiate (0.56 g., 2.62 mmoles) in 7.2 ml. of 5% sodium bicarbonate was added dropwise. After stirring for 3 hours at room temperature, the reaction mixture was quenched with water, acidified and extracted with two portions of ethyl acetate. The organic extracts were combined, dried over anhydrous magnesium sulfate, filtered and evaporated to dryness (110 mg.). The aqueous phase was adjusted to pH 7 and further crude product (100 mg.) obtained by extraction with ethyl acetate. The crude crops were combined, taken into 1N sodium hydroxide, acidified to pH 4 with acetic acid and extracted with fresh ethyl acetate. The latter organic extracts were combined and evaporated to dryness. Trituration of the residue with ether, allowing the mixture to stand until crystallization was complete, gave title product (34 mg.; m.p. 144°–146° C.).

EXAMPLE 23

5-(7-Methoxy-8-quinolyl)oxazolidin-4-one-2-thione

By the procedure of Example 19, but using adjustment to pH 7 with bicarbonate after quench and ethyl acetate for extraction, 7-methoxyquinoline-8-carbaldehyde (2.0 g., 10.7 mmoles) was converted to title product [1.17 g.; Rf 0.7 (2:1 ethyl acetate:chloroform)]. This product was not partitioned between aqueous base and ethyl acetate, nor was a second crop isolated by salting the aqueous phase and further extracting.

EXAMPLE 24

5-(7-Methoxy-8-quinolyl)oxazolidine-2,4-dione

Product of the preceding Example (0.74 g., 2.7 mmoles) was combined with 30 ml. of methanol and 15 ml. of 5% sodium bicarbonate. Sodium metaperiodate (1.15 g., 5.4 mmoles) in 15 ml. of water was added dropwise. After stirring for 3 hours at room temperature, the reaction mixture was quenched with water, acidified to pH 2–3 and extracted with two portions of ethyl acetate. The extracts were combined, dried and evaporated to dryness (360 mg.). Recrystallization from water gave purified title product (100 mg.; m.p. 207°–208° C.).

Anal. Calcd. for $C_{13}H_9N_2O_3 \cdot 1.2H_2O$: C, 59.40; H, 4.34; N, 10.66.

Found: C, 59.33; H, 4.01; N, 10.66.

EXAMPLE 25

5-Hydroxy-5-(1-methyl-2-pyrrolyl)-2,4,6-(1H,3H,5H)pyrimidinetrione

Alloxan hydrate (3.2 g., 0.02 mole) was dissolved in 50 ml. of ethanol by warming. 1-Methylpyrrole (1.6 g., 0.02 mole) was added and the mixture warmed for 5 minutes on a steam bath, while perfusing with hydrogen chloride. After standing at room temperature for 0.5 hour, the reaction mixture was evaporated to dryness and the residue triturated with water to yield title product as a solid [2.9 g.; m/e 223; Rf 0.5 (1:1 ethyl acetate:hexane/5% acetic acid)].

EXAMPLE 26

5-(1-Methyl-2-pyrrolyl)oxazolidine-2,4-dione

Product of the preceding Example (2.8 g.) was combined with 25 ml. of 1N sodium hydroxide and heated on a steam bath for 30 minutes, by which time complete dissolution had occurred. On acidification, a gum precipitated, which solidified on trituration with water (1.2 g.). Recrystallization from methanol-ether afforded purified title product [0.70 g.; m.p. 108–114 (dec); m/e 180].

Anal. Calcd. for $C_8H_8O_3N_2$:
C, 53.33; H, 4.48; N, 15.55.
Found: C, 53.16; H, 4.72; N, 15.28.

EXAMPLE 27

5-Hydroxy-5-(1-ethyl-2-pyrrolyl)-2,4,6-(1H,3H,5H)pyrimidinetrione

Potassium pyrrole [J. Chem. Soc., p. 52 (1931); 1 g.; 0.01 mole] was slurried in 5 ml. of tetrahydrofuran. Ethyl iodide (1 ml., 0.012 mole) was added, a slight exotherm being noted. The mixture was stirred for 0.5 hour, heated to reflux for 0.5 hour, cooled to room temperature, diluted with 15 ml. of water and extracted with 10 ml. of ether. The ether extract was washed with 5 ml. of water, then added to alloxan hydrate (1.6 g.) which had been dissolved in 25 ml. of ethanol by heating. The ether was boiled off and the ethanolic residue refluxed for 0.5 hour, then evaporated to a water-soluble gum. The gum was taken up in 25 ml. of ethyl acetate, washed with two 10 ml. portions of water and re-evaporated to yield title product as a gum (0.6 g., m/e 237).

EXAMPLE 28

5-(1-Ethyl-2-pyrrolyl)oxazolidine-2,4-dione

The procedure of the preceding Example was repeated on a three times scale. The initially isolated product gum (0.03 mole of the pyrimidinetrione) was stirred with 60 ml. of 1N sodium hydroxide for 0.5 hour, then acidified with conc. hydrochloric acid and extracted with ethyl acetate. The extract was filtered from insoluble impurities, and concentrated to a gum (2.2 g.). The gum was chromatographed on 100 ml. of silica gel with (1:1 ethyl acetate:hexane as eluant and tlc monitoring. Early fractions contained the desired product; these were combined and evaporated to an oil which crystallized on standing. Trituration with water gave purified title product (170 mg.; m.p. 90°–93° C.; m/e 194).

Anal. Calcd. for $C_9H_{10}O_3N_2 \cdot 0.25H_2O$:
C, 54.40; H, 5.32; N, 14.10.
Found: C, 54.37; H, 5.16; N, 13.76.

EXAMPLE 29

5-Hydroxy-5-[1-(1-butyl)-2-pyrrolyl]-2,4,6-(1H,3H,5H)pyrimidinetrione

Potassium pyrrole (3.0 g., 0.03 mole), 1-iodobutane (9.2 g., 0.05 moles) and 10 ml. of tetrahydrofuran were combined and refluxed for 1.5 hours by which time the reaction mixture had become a thick mass. The reaction mixture was diluted with 30 ml. of water and extracted with 35 ml. of ether. The ether was backwashed with water, then added to a solution of anhydrous alloxan (4.8 g., 0.03 mole) obtained by heating in 50 ml. of ethanol. The ether was distilled away, 6N hydrochloric acid (5 ml., 0.03 mole) was added, and the mixture refluxed for 3 minutes, cooled, evaporated to a gum, and triturated with water to afford title product [5.1 g.; m.p. 135 (dec); m/e 265].

EXAMPLE 30

5-[1-(1-Butyl)-2-pyrrolyl]oxazolidine-2,4-dione

Product of the preceding Example (5.1 g., 0.019 mole) was combined with 1N sodium hydroxide (38 ml., 0.038 mole) and stirred at room temperature for 10 minutes. The reaction mixture was filtered, washed with ether, cooled in an ice-water bath, acidified with conc. hydrochloric acid and extracted with three portions of ethyl acetate. The organic extracts were combined, washed with brine, dried over anhydrous sodium sulfate and evaporated to gummy solids. The latter was chromatographed on silica gel with ethyl acetate as eluant and tlc monitoring to yield partially purified product isolated as an oil (950 mg.). The latter was rechromatographed using 1:1 ethyl acetate: hexane as eluant, yielding purified title product as an oil [0.59 g.; m/e 222; Rf 0.72 (ethyl acetate)].

Anal Calcd. for $C_{11}H_{14}O_3N_2 \cdot 0.5H_2O$:
C, 57.38; H, 6.57; N, 12.17.
Found: C, 57.40; H, 6.35; N, 12.15.

EXAMPLE 31

Sodium 5-[1-(1-butyl)-2-pyrrolyl]oxazolidine-2,4-dione

Product of the preceding Example (370 mg., 1.66 mmoles) was dissolved in 5 ml. of methanol. Sodium bicarbonate (90 mg., 1.66 mmoles) was added. The resulting solution was evaporated to dryness and the solid residue triturated with ether to yield the title product [300 mg.; m.p. 123°–126° C. (dec); tlc mobility with 1:1 ethyl acetate:hexane/5% acetic acid as eluant identical with the free base form].

EXAMPLE 32

5-Hydroxy-5-(1-phenyl-2-pyrrolyl)-2,4,6-(1H,3H,5H)pyrimidinetrione

1-Phenylpyrrole (1.4 g., 0.01 mole), alloxan hydrate (1.6 g., 0.01 mole) and 50 ml. of ethanol were combined and refluxed for 15 minutes. No reaction was noted by tlc. 1N Hydrochloric acid (10 ml., 0.01 mole) was added and the acidified mixture refluxed for 15 minutes. Incomplete reaction was noted by tlc. A second portion of alloxan hydrate (1.6 g., 0.01 mole) was added and the mixture refluxed another 15 minutes, cooled and evaporated to dryness. Trituration of the residue with water gave title product [2.3 g.; m/e 285; m.p. 232°–234° C. (dec); Rf 0.3 (1:1 ethyl acetate:hexane)].

Anal. Calcd. for $C_{14}H_{11}O_4N_3 \cdot 0.25H_2O$:
C, 58.01; H, 4.00; N, 14.50.
Found: C, 57.84; H, 4.05; N, 14.56.

EXAMPLE 33

5-(1-Phenyl-2-pyrrolyl)oxazolidine-2,4-dione

The product of the preceding Example (1 g.) was heated on a steam bath for 20 minutes with 20 ml. of 1N sodium hydroxide. The mixture was then cooled in an ice-water bath, acidified with conc. hydrochloric acid and the supernatant decanted from the resulting gummy precipitate. The gum was taken up in ethyl acetate, washed with water, and evaporated to an oil (0.47 g.). The aqueous decant was also extracted with ethyl acetate, the extract back washed with water and evaporated to a second oil (0.28 g.). The two oils were combined, chromatographed on 150 ml. of silica gel with 1:1 ethyl acetate:hexane as eluant and tlc monitoring. The early, product fractions were combined, evaporated to an oil (410 mg.) and the oil crystallized from ether-hexane to yield purified title product [280 mg.; m.p. 130°–132° C.; m/e 242; Rf 0.47 (1:1 ethyl acetate: hexane)].

Anal. Calcd. for $C_{13}H_{10}O_3N_2$: C, 64.46; H, 4.16; N, 11.57.
Found: C, 64.40; H, 4.35; N, 11.56.

EXAMPLE 34

5-Hydroxy-5-(1-methyl-3-indolyl)-2,4,6,-(1H,3H,5H)pyrimidinetrione

Alloxan hydrate (1.6 g., 0.01 mole) 1-methylindole (1.3 g., 0.01 mole) and ethanol (50 ml.) were combined and the mixture refluxed for 0.5 hour, then concentrated to half-volume, diluted with water and the resulting product recovered by filtration [2.7 g., Rf 0.5 (1:1 ethyl acetate:hexane/5% acetic acid)].

EXAMPLE 35

5-(1-Methyl-3-indolyl)oxazolidine-2,4-dione

Product of the preceding Example (2 g.) was heated on a steam bath for 15 minutes with 35 ml. of 1N sodium hydroxide. The reaction mixture was cooled to room temperature, acidified to pH 1 with conc. hydrochloric acid, and decanted from a small amount of gum (130 mg.). The decant was clarified by filtration, cooled in an ice-water bath, and the resulting solids (330 mg.) recovered by filtration. The filtrate was extracted with ethyl acetate; the extract was back-washed with water and evaporated to solids (0.61 g.). The solid products were combined and recrystallized from ethyl acetate/hexane to yield title product (0.33 g.; m.p. 152°–153.5° C.).

Anal. Calcd. for $C_{12}H_{10}O_3N_2 \cdot 0.125H_2O$:
C, 61.99; H, 4.45; N, 12.05.
Found: C, 61.99; H, 4.45; N, 12.02.

EXAMPLE 36

5-Hydroxy-5-(5-bromo-3-indolyl)-2,4,6-(1H,3H,5H)pyrimidinetrione

Alloxan hydrate (1.6 g., 0.01 mole) was dissolved in 40 ml. of ethanol by heating. 5-Bromoindole (1.96 g., 0.01 mole) was added and heating near reflux continued for 15 minutes. Tlc did not indicate that reaction had occured. 1N Hydrochloric acid (10 ml.) was then added while maintaining the reaction near reflux. After 10 minutes, the reaction was concentrated to wet solids. Trituration of these wet solids with water gave the title product [3.17 g., m.p. >250° C.; Rf 0.45 (1:1 ethyl acetate:hexane/5% acetic acid); Rf 0.3 (1:5 ethyl acetate:hexane/5% acetic acid)].

EXAMPLE 37

5-(5-Bromo-3-indolyl)oxazolidine-2,4-dione

Product of the preceding Example (3.1 g.) was heated on a steam bath with 50 ml. of 1N sodium hydroxide for 15 minutes, then cooled and crude product (1.25 g.) precipitated by acidification with conc. hydrochloric acid. Chromatography on silica gel, using 1:1 ethyl acetate:hexane as eluant and tlc monitoring gave purified title product [0.41 g.; m.p. 185°–189° C.; Rf 0.55 (1:5 ethyl acetate:hexane/5% acetic acid)].

Anal. Calcd. for $C_{11}H_7O_3N_2Br$: C, 44.76; H, 2.38; N, 9.49.
Found: C, 45.10; H, 2.68; N, 9.58.

EXAMPLE 38

5-Hydroxy-5-(2-thiazolyl)-2,4,6-(1H,3H,5H)pyrimidinetrione

Thiazole (1.7 g., 0.02 mole) was dissolved in tetrahydrofuran (35 ml.) and cooled to −60° C. Butyllithium (9 ml. of 2.4M in hexane, 0.0216 mole) was added dropwise over 20 minutes, and the reaction mixture stirred for an additional 30 minutes at −60° C. In this manner 2-thiazolyllithium was formed. Anhydrous alloxan (3 g., 0.021 mole) was dissolved in 20 ml. of tetrahydrofuran and added dropwise over 20 minutes, keeping the temperature at −60° C. The stirred reaction mixture was warmed to room temperature over 30 minutes, then recooled to 0° C. 1N Hydrochloric acid (25 ml.) was added portion wise and the quenched reaction mixture extracted with 50 ml. of ethyl acetate. The ethyl acetate extract was back-washed with 15 ml. of water, dried over anhydrous sodium sulfate, filtered and evaporated to yield title product [1.9 g.; m/e 227; Rf 0.4 (1:1 ethyl acetate:hexane/5% acetic acid)].

By the same procedure, oxazole is converted to 5-hydroxy-5-(2-oxazolyl)-2,4,6-(1H,3H,5H)pyrimidinetrione.

EXAMPLE 39

5-(2-Thiazolyl)oxazolidine-2,4-dione

Title product of the preceding Example (1.37 g.) was stirred at room temperature with 24 ml. of 1N sodium hydroxide. The reaction mixture was allowed to stand for 25 minutes, acidified with 3 ml. of glacial acetic acid and extracted with two 50 ml. portions of ethyl acetate. The extracts were separately dried over sodium sulfate, filtered and evaporated to solids, the first yielding 184 mg., the second 85 mg. These solids were combined and chromatographed on 50 ml. of silica gel with 1:1 ethyl acetate:hexane/5% acetic acid as eluant and tlc monitoring. Clean product fractions were combined, evaporated to dryness and the residue triturated with hexane to yield purified title product (155 mg.; m.p. 150°-152° C.).

Anal. Calcd. for $C_6H_4O_3N_2S$: C, 39.13; H, 2.19; N, 15.21.

Found: C, 39.53; H, 2.52; N, 14.95.

By the same procedure, the other product of the preceding Example is converted to 5-(2-oxazolyl)oxazolidine-2,4-dione.

EXAMPLE 40

5-Hydroxy-5-(2-benzthiazolyl)-2,4,6-(1H,3H,5H)pyrimidinetrione

By the procedure of Example 38, benzthiazole (2.7 g., 0.02 moles) was converted to its 2-lithio derivative and then reacted with anhydrous alloxan to yield title product, initially isolated as an oil. The latter was crystallized from ether-hexane [2.2 g.; Rf 0.55 (1:1 ethyl acetate:hexane/5% acetic acid)].

EXAMPLE 41

5-(2-Benzthiazolyl)oxazolidine-2,4-dione

Product of the preceding Example 2.15 g.) was stirred with 30 ml. of 1N sodium hydroxide for 30 minutes. The reaction mixture was extracted with ether and product (0.46 g.) precipitated by acidification of the aqueous layer with 6N hydrochloric acid. Chromatography on 50 ml. of silica gel with 1:1 ethyl acetate:hexane/5% acetic acid as eluant and tlc monitoring, followed by recrystallization from acetone-isopropyl ether gave purified title product [110 mg., m.p. 214°-216° C. (dec)].

Anal. Calcd. for $C_{10}H_6O_3N_2S$: C, 51.29; H, 2.58; N, 11.96

Found: C, 51.51; H, 2.99; N, 12.21.

EXAMPLE 42

2-(6-Chloro-8-chromanyl)-2-trimethylsiloxyethanenitrile

6-Chlorochroman-8-carbaldehyde (7 g., 0.036 mole) in 70 ml. of methylene chloride was cooled to 0°-5° C. Zinc iodide (100 mg.) was added, followed by the dropwise addition of trimethylsilylcarbonitrile (4.26 g., 0.043 mole). The reaction mixture was stirred at room temperature for 64 hours, then washed in sequence with three portions of saturated sodium bicarbonate and one of brine, dried over anhydrous magnesium sulfate, filtered and evaporated to yield title product as an oil [9.5 g.; ir($CH_2Cl_2$) 2857, 1479, 1215, 1190, 1060 cm$^{-1}$].

EXAMPLE 43

Ethyl 1-(6-Chloro-8-chromanyl)-1-hydroxymethanecarboximidate Hydrochloride

To cold (0°-5° C.), saturated ethanolic hydrogen chloride (250 ml.) there was added, in a dropwise manner, product of the preceding Example (9.29 g.) in 15 ml. of ethanol, keeping the temperature below 10° C. The mixture was stirred at 0°-5° C. for 35 minutes and then evaporated to an oil. Crystallization from ethanol-ether gave title product [5.7 g.; m.p. 125°-127° (dec); m/e 271/269].

EXAMPLE 44

5-(6-Chloro-8-chromanyl)oxazolidine-2,4-dione

Product of the preceding Example (5.4 g., 18.6 mmoles) was suspended in 250 ml. of tetrahydrofuran, cooled in an ice-water bath, and triethylamine (6.01 g., 0.06 mole) added. The cold mixture was perfused with phosgene for 30 minutes, stirred at room temperature for 1 hour and then poured into 1 liter of crushed ice. The quenched reaction mixture was extracted with three portions of methylene chloride. The combined extracts were washed with brine, dried over anhydrous magnesium sulfate and evaporated to solids. The residue was recrystallized from toluene to yield purified title product (3.28 g., m.p. 170°-172° C., m/e 269/267).

Anal. Calcd. for $C_{12}H_{10}O_4NCl$: C, 53.84; H, 3.77; N, 5.23

Found: C, 53.73; H, 3.83; N, 5.48.

EXAMPLE 45

2-(6-Fluoro-8-chromanyl)-2-trimethylsiloxyethanenitrile

By the procedure of Example 42, 6-fluorochroman-8-carbaldehyde (3.2 g., 0.0178 mole) was converted to title product as an oil [4.51 g., m/e 279; ir (CHCl$_2$) 1498, 1205, 1066 cm$^{-1}$].

EXAMPLE 46

Ethyl 1-(6-Fluoro-8-chromanyl)-1-hydroxymethanecarboximidate Hydrochloride

Using a reaction time of 1 hour at 0°-5° C., the procedure of Example 43 was employed to convert product of the preceding Example (4.4 g.) to title product 4.1 g.; m.p. 124°-126° C. (dec); m/e 253].

EXAMPLE 47

5-(6-Fluoro-8-chromanyl)oxazolidine-2,4-dione

By the procedure of Example 44, product of the preceding Example (3.9 g., 0.0134 mole) was converted to crude title product. Crude solids were taken into 1N sodium hydroxide and extracted with two portions of ether. Product was reprecipitated by adding the basic aqueous layer slowly to excess 3N hydrochloric acid. Recrystallization from toluene gave purified title product [2.73 g.; m.p. 174°-176° C.; m/e 251].

Anal. Calcd. for $C_{12}H_{10}O_4NF$: C, 57.37; H, 4.01; N, 5.58.

Found: C, 57.74; H, 3.91; N, 5.40.

EXAMPLE 48

2-(5-Chloro-2,3-dihydro-7-benzo[b]furanyl)-2-trimethylsiloxyethanenitrile

5-Chloro-2,3-dihydrobenzo[b]furan-7-carbaldehyde (900 mg., 4.9 mmoles) was dissolved in 25 ml. of ether. Zinc iodide (20 mg.) and then trimethylsilylcarbonitrile (970 mg., 9.8 mmoles) were added and the mixture stirred 16 hours at room temperature, then diluted with 50 ml. ether, washed with three portions of saturated sodium bicarbonate and one of brine, dried over anhydrous magnesium sulfate, filtered and evaporated to yield title product as an oil [1.4 g.; m/e 283/281; ir(CHCl$_2$) 1479, 1457, 1435, 1180, 866, 848 cm$^{-1}$].

By the same method 5-fluoro-2,3-dihydrobenzo[b]furan-7-carbaldehyde is converted to 2-(5-fluoro-2,3-dihydro-7-benzo[b]furanyl)-2-trimethylsiloxyethanenitrile.

EXAMPLE 49

Ethyl 1-(5-Chloro-2,3-dihydro-7-benzo[b]-furanyl)-1-hydroxymethanecarboximidate Hydrochloride By the procedure of Example 43, title compound of the preceding Example (1.37 g.) was converted to title product. The initially isolated solids were repulped twice in ether to obtain purified product [1.28 g.; m.p. 149°-152° C. (dec); m/e 257/255; ir(KBr) 3162, 2875, 1650, 1524, 1458 cm$^{-1}$].

By the same method the fluoro compound of the preceding Example is converted to ethyl 1-(5-fluoro-2,3-dihydro-7-benzo[b]furanyl)-1-hydroxymethanecarboximidate hydrochloride.

EXAMPLE 50

5-(5-Chloro-2,3-dihydro-7-benzo[b]furanyl)oxazolidine-2,4-dione

By the procedure of Example 44, title compound of the preceding Example (1.1 g.) was converted to toluene recrystallized title product [630 mg.; m.p. 197°-199° C.; m/e 255/253; ir(KBr) 3084, 1833, 1810, 1746 cm$^1$].

By the same procedure the fluoro analog of the preceding Example is converted to 5-(5-fluoro-2,3-dihydro-7-benzo[b]furanyl)oxazolidine-2,4-dione.

EXAMPLE 51

2-(3-Methyl-5-isoxazolyl)-2-tr-imethylsilylethanenitrile

By the procedure of Example 42, 3-methylisoxazole-5-carbaldehyde (3.4 g., 0.032 mole) was converted to title product, isolated as an oil (6.5 g., no aldehyde proton by nmr).

By the same method, isothiazole-5-carbaldehyde is converted to 2-(5-thiazolyl)-2-trimethylsilylethanenitrile and 5-methylisoxazole-3-carbaldehyde (Kane et al., Japan 62/17,572) is converted to 2-(5-methyl-3-isoxazolyl)-2-trimethylsilylethanenitrile.

EXAMPLE 52

Ethyl 1-Hydroxy-1-(3-methyl-5-isoxazolyl)-methanecarboximidate Hydrochloride

Title product of the preceding Example (6.5 g.) was dissolved in cold, saturated ethanolic hydrogen chloride (50 ml.) and held at 5° C. for 16 hours. Title product was recovered by filtration (3.3 g., m.p. 119°-121° C.

By the same method, the other products of the preceding Example are converted to ethyl 1-hydroxy-1-(5-isothiazolyl)methanecarboximidate hydrochloride and ethyl 1-hydroxy-1-(5-methyl-3-isoxazolyl)methanecarboximidate hydrochloride.

EXAMPLE 53

5-(3-Methyl-5-isoxazolyl)oxazolidine-2,4-dione

By the procedure of Example 44, title product of the preceding Example (2.2 g.), was converted to title product. After quench into crushed ice, the product was extracted into ether, the combined extracts dried and evaporated to an oil (1.4 g.). Further extraction with ethyl acetate and evaporation gave additional oil (0.4 g.). The oils were combined and partitioned between 25 ml. of 1N sodium hydroxide and 25 ml. of ether. The basic aqueous phase was separated, acidified with conc. hydrochloric acid and extracted with 25 ml. of ethyl acetate. The ethyl acetate extract was back-washed with water, evaporated to dryness, the residue triturated with ether (146 mg., m.p. 173°-175° C.). The ether triturate was evaporated to dryness and triturated with fresh ether (238 mg., m.p. 175°-177° C.).

By the same method, the other products of the preceding Example are converted to 5-(5-isothiazolyl)oxazolidine-2,4-dione and 5-(5-methyl-3-isoxazolyl)oxazolidine-2,4-dione.

EXAMPLE 54

5-(5-Chloro-2-ethoxy-3-pyridyl)oxazolidine-2,4-dione 5-(2-Ethoxy-3-pyridyl)oxazolidine-2,4-dione (125 mg.) was suspended in 100 ml. of water and dissolved by warming to 56° C. Chlorine was bubbled into the warm solution for 30 minutes, during which time the temperature slowly dropped to 34° C. and a precipitate formed. The reaction mixture was flushed with nitrogen for 30 minutes and crude product recovered by filtration (101 mg., m.p. 119°-124° C.). Two recrystallizations from 2:1 ethanol:water gave purified title product [24 mg.; m.p. 145°-147° C.; Rf 0.56 (1:1 ethyl acetate:chloroform); m/e 256].

By the same procedure, substituting 10% fluorine in nitrogen, 5-(2-ethoxy-3-pyridyl)oxazolidine-2,4-dione is converted to 5-(5-fluoro-2-ethoxy-3-pyridyl)oxazolidine-2,4-dione.

PREPARATION 1

2-Ethoxy-3-pyridinecarboxylic Acid

Sodium ethoxide was prepared by adding sodium (1.4 g., 0.06 mole) portion wise to 50 ml. of anhydrous ethanol. The solution was diluted with 20 ml. of ethanol and 4.5 g. of 2-chloropyridine-3-carboxylic was added. The reaction mixture was heated in a steel pressure vessel at 170° C. for 6 hours. The vessel was cooled and the contents evaporated to dryness in vacuo. The residue was taken up in 150 ml. of water and acidified to constant pH 4.5. The water solution was saturated with salt and extracted with four portions of ethyl acetate. The combined ethyl acetate layers were back washed with brine, dried over anhydrous magnesium sulfate, filtered and evaporated to yield title product (4.33 g., m.p. 85°-88° C.).

PREPARATION 2

2-Methoxy-3-pyridinecarboxylic Acid

A stainless steel stirred autoclave was charged sequentially with methanol (2.8 l.), sodium methoxide (259 g.) (in portions, keeping the temperature less than 35° C.), and 2-chloro-3-pyridinecarboxylic acid (190 g.). The autoclave was sealed and the reaction mixture heated at 110° C. (50 psig) for 48 hours. The reaction mixture was cooled to 25° C. and discharged from the autoclave. Solids were recovered by filtration. Concentration of the filtrate gave a second crop. These process steps were repeated until virtually all of the methanol had been removed. The several crops of solids were combined, taken up in 2.5 liters of water and acidified with conc. hydrochloric acid to pH 2.7 keeping the temperature below 20° C. The precipitated product was granulated for 30 minutes at 15° C. and recovered by filtration (141 g.). Purified title product was obtained by recrystallization from ethyl acetate-hexane (120.5 g., m.p. 148°–150° C.).

PREPARATION 3

Ethyl 2-(6-Chloro-8-quinolyl)-2-oxoacetate

8-Bromo-6-chloroquinoline [J. Het. Chem. 6, pp. 243–245 (1969); 6 g., 0.025 mole] in 50 ml. of tetrahydrofuran was added dropwise over a 10 minute period to a mixture of butyl lithium (2.3M in hexane, 12.2 ml., 0.028 mole) and 40 ml. of tetrahydrofuran held at −70° C. After an additional 30 minutes at this temperature, a cold (0° C.) solution of diethyl oxalate (14.6 g., 0.10 mole) in 50 ml. of tetrahydrofuran was added dropwise. The reaction mixture was maintained at 0° C. for 1 hour, then quenched at 0°–5° C. with glacial acetic acid (17 ml.) in 50 ml. of tetrahydrofuran. After warming to room temperature the quenched mixture was poured into 500 ml. of water and then diluted with 500 ml. of ethyl acetate and 500 ml. of saturated sodium bicarbonate. The organic layer was separated, washed with 500 ml. of fresh bicarbonate, dried over anhydrous magnesium sulfate, filtered, and evaporated to an oil. Trituration with two 100 ml. portions of hexane gave the title product (2.3 g., m.p. 107°–110° C.; m/e 265/263).

PREPARATION 4

Ethyl 2-(6-Chloro-8-quinolyl)-2-hydroxyacetate

Sodium borohydride (2.5 g., 0.066 mole) was dissolved in 300 ml. of ethanol at 10° C. and added in one portion to a 10° C. solution of product of the preceding Preparation (2.0 g., 0.0076 mole) in 200 ml. of ethanol. After a few minutes, the reaction mixture was diluted with 750 ml. of ethyl acetate and 750 ml. of water. The aqueous layer was extracted with 250 ml. of fresh ethyl acetate. The organic layers were combined, washed with three 250 ml. portions of brine, dried over anhydrous magnesium sulfate, filtered and evaporated to yield title product, initially an oil which crystallized on standing (1.87 g.; m.p. 121°–124° C., m/e 267/265).

PREPARATION 5

Ethy 2-(6-Fluoro-8-quinolyl)-2-oxoacetate

By the procedure of Preparation 3, 8-bromo-6-fluoroquinoline [J. Het. Chem., 6, pp. 243–245 (1969); 4.5 g., 0.02 mole] was converted to hexane triturated title product (1.6 g.; m.p. 114°–117° C.).

PREPARATION 6

Ethyl 2-(6-Fluoro-8-quinolyl)-2-hydroxyacetate

By the procedure of Preparation 4, product of the preceding Preparation (1.5 g., 6.1 mmoles) was converted to title product. The product, initially obtained. as a turbid oil, was taken back up in ethyl acetate, washed with brine, dried, filtered and evaporated to an oil which rapidly crystallized (1.23 g., m.p. 84°–87° C.).

PREPARATION 7

6-Hydroxyquinoline-5-carbaldehyde

Sodium hydroxide (25 g.) was dissolved in 35 ml. of water with cooling, 6-hydroxyquinoline (5 g.) in 15 ml. of chloroform was added and the reaction mixture heated to reflux (about 90° C.) for 12 hours, during which two further 15 ml. portions of chloroform were added—one after 2 hours and the other after 6 hours. The reaction mixture was cooled and crude product recovered by filtration. The crude was dissolved in 125 ml. of hot water treated with activated carbon, filtered hot, cooled and acidified with acetic acid and filtered to yield title product [2.5 g.; m.p. 136°–137° C.; m/e 173; pnmr/CDCl$_3$ shows aldehyde proton at 10.5 ppm and aromatic protons at 7.2–9.4 ppm.].

PREPARATION 8

6-Methoxyquinoline-5-carbaldehyde

Product of the preceding Preparation (1.7 g., 9.8 mmoles) in 85 ml. of acetone was combined with potassium carbonate (1.21 g., 8.8 mmoles). Dimethyl sulfate (0.83 ml., 8.8 mmoles) was added and the mixture stirred at room temperature for 16 hours. Additional potassium carbonate (0.34 g., 2.5 mmole) and dimethyl sulfate (0.23 ml., 2.5 mmole) were added and the mixture stirred 4 more hours at room temperature and then 3 hours at 60° C. The reaction mixture was cooled to room temperature, salts removed by filtration, and the filtrate evaporated to dryness. The residue was taken up in ethyl acetate, washed sequentially with two portions of 1N ammonium hydroxide, one of water and one of brine, dried over anhydrous magnesium sulfate, filtered and evaporated to yield title product [0.78 g.; Rf 0.35 (2:1 ethyl acetate:chloroform); pnmr/CDCl$_3$/delta (ppm): 4.2 (s, 3H), 7.4–9.1 (m, 5H), 10.3 (s, 1H)].

PREPARATION 9

7-Hydroxyquinoline-8-carbaldehyde

By the procedure of the Preparation 7, 7-hydroxyquinoline (5 g.) was converted to title product (3.3 g., m.p. 127°–130° C.; m/e 173; pnmr/CDCl$_3$ shows aldehyde proton at 10.8 ppm, aromatic protons at 7.0–8.9 ppm.

PREPARATION 10

7-Methoxyquinoline-8-carbaldehyde

By the procedure of Preparation 8, the product of the preceding Preparation (3.3 g., 19 mmoles) was converted to title product [2.1 g., pnmr/CDCl$_3$/delta (ppm): 4.1 (s, 3H), 7.5–9.0 (m, 5H), 11.2 (s, 1H)].

PREPARATION 11

6-Chlorochroman

Mossy zinc (75 g.), 7.5 g. of mercuric chloride, 125 ml. of water and 4 ml. of conc. hydrochloric acid were combined, shaken for 5 minutes, allowed to settle, and liquids decanted from the resulting amalgamated zinc. A mixture of 100 ml. of water and 126 ml. of conc. hydrochloric acid and then 6-chloro-4-chomanone (15 g.) were added to the metal, and the mixture refluxed for 1.5 hours, cooled to room temperature, decanted from the zinc and the decant extracted with three portions of ether. The combined extracts were dried over anhydrous magnesium sulfate, filtered and concentrated to an oil (14 g.). The oil was chromatographed on 400 g. of silica gel using 9:1 hexane: ether as eluant tlc monitoring and 15 ml. fractions. Clean product fractions were combined and evaporated to yield title product as an oil [8.72 g.; pnmr/CDCl$_3$/delta (ppm) 2.0 (m, 2H), 3.7 (t, 2H), 4.1 (t, 2H), 6.9 (m, 3H); m/e 170/168; Rf 0.88 (2:1 hexane: ether)].

PREPARATION 12

6-Chlorochroman-8-carbaldehyde

Product of the preceding Preparation (8.6 g., 0.051 mole) in 75 ml. of methylene chloride was cooled in an ice-water bath. Titanium tetrachloride (19.34 g., 11.2 ml., 0.102 mole) was added, followed by the dropwise addition of 1,1-dichloromethyl methyl ether (6.2 g., 0.054 mole). The reaction mixture was stirred at 0° for 30 minutes, then slowly poured into 400 ml. of saturated sodium bicarbonate. The aqueous phase was extracted with three fresh portions of methylene chloride. The combined organic layers were washed with brine, dried over anhydrous magnesium sulfate, filtered and evaporated to yield title product [7.9 g.; m.p. 83°–86° C.; pnmr/CDCl$_3$/delta (ppm) 2.0 (m, 2H), 2.8 (t, 2H), 4.2 (t, 2H), 7.1–7.5 (m, 2H), 10.2 (s, 1H), m/e 198/196].

PREPARATION 13

6-Fluorochroman

By the procedures of Preparation 11, 6-fluoro-4-chromanone (15 g.) was converted to chromatographed 6-fluorochroman [5.7 g.; oil; pnmr/CDCl$_3$/delta (ppm) 2.0 (m, 2H), 3.8 (t, 2H), 4.1 (t, 2H), 6.8 (m, 3H); Rf 0.68 (2:1 hexane:ether); m/e 152].

PREPARATION 14

6-Fluorochroman-8-carbaldehyde

By the procedures of Preparation 12, the product of the preceding Preparation (5.5 g., 0.036 mole) was converted to title product initially isolated as a viscous oil which was crystallized from hexane (3.4 g.; m.p. 54°–57° C.; m/e 180).

PREPARATION 15

3-Methyl-5-isoxazolecarboxamide

3-Methyl-5-isoxazolecarboxylic acid (20 g.) was refluxed for 10 hours in 350 ml. of thionyl chloride, then stirred at room temperature for 16 hours, clarified by filtration and evaporated to an oil. The oil was multiply triturated with hot hexane, and the combined hexane triturates evaporated to yield acid chloride (16.2 to 21 g.) as a solid.

With stirring, acid chloride prepared in the manner (35 g.) was added portionwise to 300 ml. of conc. ammonium hydroxide at room temperature. After granulating for 1 hour, title product was recovered by filtration (24.2 g., m.p. 180°–182° C.).

PREPARATION 16

3-Methyl-5-isoxazolecarbonitrile

Product of the preceding Preparation (5 g.) was mixed thoroughly with phosphorous pentoxide (10 g.) and placed in an oil bath preheated to 140°. The bath temperature was increased to 200° C. and title product recovered by distillation in vacuo [2.9 g., ir(film) nitrile band at 2220 cm$^1$, no amide peak in the 1700 cm$^{-1}$ region].

PREPARATION 17

3-Methyl-5-isoxazolecarbaldehyde

Product of the preceding Preparation (1.08 g., 0.01 mole) was dissolved in 25 ml. of ether and cooled to −40° C. Diisobutylaluminum hydride (12 ml. of 1M in hexane, 0.012 mole) was added at −40° C. over a 15 minute period. The mixture was stirred at −30° to −35° C. for 10 minutes. Keeping the temperature at −20° C., 60 ml. of ethyl acetate was added. Keeping the temperature at −25° C., methanol (15 ml.) was added dropwise, and keeping the temperature below −20° C., 3 ml. of 6N hydrochloric acid was added. The reaction mixture was warmed to 5° C. and the organic phase washed with 25 ml. of water and evaporated to an oil. The oil was chromatographed on 50 ml. of silica gel using 1:1 ether:hexane as eluant. Product fractions were combined and evaporated to yield title product (0.42 g.; m.p. 39°–41° C.). A small sample further purified by sublimation had m.p. 43°–45° C.

PREPARATION 18

5-Chlorobenzo[b]furan-2-carboxylic Acid

5-Chlorosalicylaldehyde (31.3 g., 0.2 mole) was dissolved in 200 ml. of 2-butanone. Potassium carbonate (82.9 g., 0.6 mole) and then diethyl 2-bromomalonate (95.6 g., 0.4 mole) were added and the mixture heated to reflux for five hours, then cooled, filtered from salts, and concentrated to an oil. The oil was partitioned between 500 ml. of 10% sulfuric acid and 500 ml. of ether. The aqueous layer was extracted with two 250 ml. portions of fresh ether. The combined organic layers were washed with brine, dried over anhydrous magnesium sulfate, filtered and concentrated to a second oil. The second oil was dissolved in 400 ml. of 10% ethanolic potassium hydroxide, heated at reflux for 1 hour and concentrated to solids. The solids were dissolved in 1500 ml. of water, filtered from trace insoluble matter, acidified with 6N hydrochloric acid and precipitated solids recovered by filtration. Purified title product was obtained by repulping the solids in 1 liter of water (19 g., m.p. 259°–262° C., m/e 198/196).

By the same procedure, 5-fluorosalicylaldehyde and 6-chlorosalicylaldehyde are converted, respectively, to 5-fluorobenzo[b]furan-2-carboxylic acid and 6-chlorobenzo[b]furan-2-carboxylic acid.

PREPARATION 19

5-Chlorobenzo[b]furan

Title compound of the preceding Preparation (7.8 g.) was combined with copper powder (700 mg.) and quinoline (50 ml.) and the mixture heated to reflux for 50 minutes, then cooled to room temperature and diluted with 500 ml. of ether. Insolubles were removed by filtration and the filtrate washed in sequence with five 200 ml. portions of 2N hydrochloric acid and one of brine, dried over anhydrous magnesium sulfate and concentrated to an oil (6.2 g.). The oil was chromatographed through 200 g. of silica gel using ether as eluant and 300 ml. fractions. Fractions 1 and 2 were combined and evaporated to yield title product as an oil (6.1 g.).

By the same procedure the other benzofurancarboxylic acids of the preceding Preparation are converted to 5-fluorobenzo[b]furan and 6-chlorobenzo[b]furan.

PREPARATION 20

5-Chloro-2,3-dihydrobenzo[b]furan

Pd/C (5%, 12.2 g.) in 400 ml. of acetic acid was prehydrogenated at atmospheric pressure and 25° C. Title compound of the preceding Preparation (6.1 g.) in 100 ml. of acetic acid was added and hydrogenation continued until slightly more than 1 equivalent of hydrogen had been consumed. Catalyst was recovered by filtration over diatomaceous earth. The filtrate was neutralized with saturated potassium carbonate and extracted with four 200 ml. portions of ether. The combined extracts were washed with brine, dried over anhydrous magnesium sulfate, filtered and evaporated to an oil. The oil was chromatographed on 400 g. silica gel using hexane-3% ether as eluant, 15 ml. fractions and tlc monitoring. Pure product fractions 70-90 were combined and evaporated to yield title product [2.15 g.; oil; Rf 0.32 (hexane); m/e 156/154].

By the same procedure, the other benzofurans of the preceding Preparation are converted to 5-fluoro-2,3-dihydrobenzo[b]furan and 6-chloro-2,3-dihydrobenzo[b]furan.

PREPARATION 21

5-Chloro-2,3-dihydrobenzo[b]furan-7-carbaldehyde

By the procedure of Preparation 12, title compound of the preceding Preparation (2.1 g.) was converted to crude product contaminated with an isomeric aldehyde. Purified title product was obtained by digesting the crude product in 50 ml. of boiling hexane, filtering and cooling the filtrate [0.93 g.; m.p. 79°-81° C.; Rf 0.55 (chloroform); m/e 184/182].

By the same method the 5-fluoro compound of the preceding Preparation is converted to 5-fluoro-2,3dihydrobenzo-[b]furan-7-carbaldehyde.

By the method of Preparation 3, the 6-chloro compound is converted to ethyl 2-(6-chloro-2,3-dihydro-7-benzo[b]furanyl)-2-oxoacetate; then by the method of Preparation 4 to ethyl 2-(6-chloro-2,3-dihydro-7-benzo[b]furanyl)-2-hydroxyacetate.

PREPARATION 22

7-Chloroquinoline-8-carbaldehyde

7-Chloro-8-methylquinoline (1 g.) [Bradford et al., J. Chem. Soc., p. 437 (1947)] is dissolved in 20 ml. of benzene and brominated with one equivalent of N-bromosuccinimide in the presence of catalytic amounts of peroxide. The product, 7-chloro-8-(bromomethyl)-quinoline is isolated by evaporation.

The bromo compound is solvolyzed to 7-chloro-8-(hydroxymethyl)quinoline by warming with excess alcoholic potassium hydroxide. To isolate the product, the reaction mixture is neutralized with hydrochloric acid, salts separated by filtration and the filtrate evaporated to dryness.

The alcohol (1 g.) is dissolved in 10 ml. of methylene chloride and added dropwise to a slurry of 1.5 equivalents of pyridinum chlorochromate in 20 ml. of methylene chloride. The exothermic reaction is controlled by rate of addition, use of a reflux condenser and occasional cooling in a cooling bath. The reaction mixture is diluted with ether, and the supernatant separated by decantation and filtration. The product is purified by filtration through a short magnesium silicate column with ether as eluant and isolated by removal of the solvent in vacuo.

I claim:

1. A compound of the formula

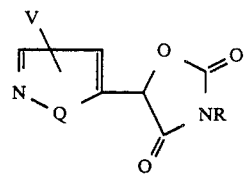

or a pharmaceutically acceptable salt thereof; wherein
R is hydrogen, (C$_1$–C$_4$)-alkanoyl, benzoyl, (C$_2$–C$_4$)-carbalkoxy, (C$_1$–C$_3$)-alkylcarbamoyl, (C$_5$–C$_7$)-cycloalkylcarbamoyl or di(C$_{1}$ –$_{C3}$)-alkylcarbamoyl;
Q is sulfur or oxygen; and
V is hydrogen or (C$_1$–C$_3$)-alkyl.

2. A compound of claim 1 wherein R is hydrogen and Q is oxygen.

3. The compound of claim 2 having the formula

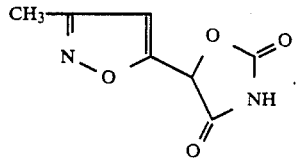

4. A method of lowering the blood glucose in a hyperglycemic mammal which comprises administering a blood glucose lowering amount of a compound of claim 1.

* * * * *